United States Patent [19]  [11] 4,177,212
Poppelsdorf  [45] Dec. 4, 1979

[54] PROCESS FOR PREPARING BIS(N,N-DIALKYLAMINO)ALKYL ETHERS EMPLOYING SULFUR OXYCHLORO-CONTAINING COMPOUNDS

[75] Inventor: Fedor Poppelsdorf, Charleston, W. Va.

[73] Assignee: Union Carbide Corporation, New York, N.Y.

[21] Appl. No.: 901,812

[22] Filed: May 1, 1978

[51] Int. Cl.² .................. C07C 85/24; C07C 93/10
[52] U.S. Cl. .................. 260/584 R; 260/459 R; 260/692; 260/584C
[58] Field of Search ........... 260/584 R, 614 R, 584 C, 260/692

[56] References Cited
U.S. PATENT DOCUMENTS

| 516,766 | 3/1894 | Krafft et al. | 260/614 R |
| 1,674,891 | 6/1928 | Duchange | 260/614 R |
| 2,796,443 | 6/1957 | Meyer et al. | 260/584 R X |
| 4,083,873 | 4/1978 | Sherrod et al. | 260/584 R |

FOREIGN PATENT DOCUMENTS 2525636  11/1975  Fed. Rep. of Germany ...... 260/584 R Primary Examiner—Patrick Garvin
Assistant Examiner—John Doll
Attorney, Agent, or Firm—Richard J. Gallagher

[57] ABSTRACT

A process is provided for producing bis-(N,N-dialkylamino)alkyl ethers of the formula $(R_2NR')_2O$, wherein R is a methyl or ethyl group and R' is a bivalent alkylene group having from 2 to 3 carbon atoms. The novel process is effected by a two-step, "one pot" reaction that utilizes a chloro-containing compound selected from the group consisting of sulfuryl chloride, thionyl chloride and chlorosulfonic acid together with $R_2NR'ONa$ as reactants, wherein R and R' are defined above. The resulting bis-ethers are useful as catalysts in the production of polyurethanes, especially cellular polyurethanes.

17 Claims, No Drawings

PROCESS FOR PREPARING BIS(N,N-DIALKYLAMINO)ALKYL ETHERS EMPLOYING SULFUR OXYCHLORO-CONTAINING COMPOUNDS

FIELD OF THE INVENTION

This invention relates to a process for producing bis-(N,N-dialkylamino)alkyl ethers of the formula $(R_2NR')_2O$, wherein R is a methyl or ethyl group and R' is a bivalent alkylene group having from 2 to 3 carbon atoms. These ethers are useful as catalysts in the production of polyurethanes, especially cellular polyurethanes.

BACKGROUND AND DESCRIPTION OF THE PRIOR ART

Bis[beta(N,N-dimethylamino)alkyl] ethers, including the commercially important bis[2-(N,N-dimethylamino)ethyl] ether ("BDMEE"), are known to be valuable polyurethane catalysts, particularly in the production of flexible polyurethane foam. By way of illustration, the production of polyurethane foam by reacting an organic isocyanate with an active hydrogen-containing compound (polyol) in the presence of a bis[-beta(N,N-dimethylamino)alkyl] ether catalyst is disclosed in U.S. Pat. No. 3,330,782.

Several processes for the production of bis[beta(N,N-dimethylamino)ethyl] ethers, including BDMEE, are known. One process utilizes di(2-chloroethyl) ether as a reactant as disclosed in U.S. Pat. Nos. 3,400,157 and 3,426,072. However, there are several disadvantages associated with the use of di(2-chloroethyl) ether, including (a) the need to employ comparatively expensive corrosion resistant equipment because of the presence of chlorides in the reaction mixture, (b) disposal problems associated with by-product chlorides, and (c) the relatively high cost and lack of ready availability of di(2-chloroethyl) ether. Another process for the production of bis[beta-(N,N-dimethylamino)alkyl] ethers involves reacting a beta-(N,N-dimethylamino) alkanol, a beta-(N,N-dimethylamino) alkyl chloride, and an alkali metal hydroxide using a modified Williamson synthesis as disclosed in U.S. Pat. No. 3,480,675. However, this modified Williamson synthesis has several disadvantages, including (a) several solids-handling steps, (b) a discontinuous mode of operation, (c) disposal problems associated with by-product sodium chloride, and (d) one of the reactants, 2-dimethylaminoethyl chloride, used in the production of BDMEE is an unstable liquid and is also a vesicant which requires special handling. A further process for the production of BDMEE comprises reacting trimethylamine with 2-[2-(N,N-dmethylamino)ethoxy] ethanol in the presence of a nickel catalyst under superatmospheric pressure as disclosed in U.S. Pat. No. 3,957,875. However, this process requires the use of a costly high-pressure reactor and provides product yields that leave room for improvement. Accordingly, it is desirable to provide a process for the production of bis-(N,N-dialkylamino)alkyl ethers, including BDMEE, that does not possess the disadvantages associated with the above-mentioned processes.

OBJECTS

It is an object of this invention to provide a process for the production of bis-(N,N-dialkylamino)alkyl ethers, including BDMEE, from relatively inexpensive, readily available starting materials.

It is a further object of this invention to provide a process for the production of bis-(N,N-dialkylamino)alkyl ethers that gives improved product yields.

It is another object of this invention to provide a process for the production of bis-(N,N-dialkylamino)alkyl ethers that is essentially a "one pot" process in order to minimize the need for material transfer.

It is still another object of the invention to provide a process for the production of bis-(N,N-dialkylamino)alkyl ethers by a liquid phase reaction that avoids the necessity of solids handling steps.

These and other objects will become apparent from a reading of the following detailed specification.

SUMMARY OF THE INVENTION

The present invention relates to a process for producing bis-(N,N-dialkylamino)alkyl ethers having the formula $(R_2NR')_2O$, wherein R is a methyl or ethyl group and R' is a bivalent alkylene group having from 2 to 3 carbon atoms. The process of the invention comprises:

(a) reacting sodio N,N-dialkylaminoalkoxide of the formula $R_2NR'ONa$, wherein R and R' are defined above, with a sulfur oxychloro-containing compound selected from the group consisting of sulfuryl chloride, thionyl chloride and chlorosulfonic acid in an amount of from about 0.10 to about 0.50 (preferably from about 0.20 to about 0.35) moles of said sulfur oxychloro-containing compound per mole of N,N-dialkylaminoalkoxide at a temperature of from about 15° C. to about 115° C. (preferably from about 25° C. to about 30° C.) in the presence of:

(I) an organic diluent/dispersant in an amount ranging from 0 to about 60 (preferably from about 40 to about 60) weight percent based on the amount of sodio N,N-dialkylaminoalkoxide and N,N-dialkylaminoalkanol employed, and (II) an N,N-dialkylaminoalkanol of the formula $R_2NR'OH$, wherein R and R' are defined above, that is present in an amount such that the molar ratio of sodio N,N-dialkylaminoalkoxide to N,N-dialkylaminoalkanol ranges from about 1:1 to about 1:5, to produce an intermediat reaction product mixture, (b) heating the intermediate reaction product mixture from step (a) to an elevated temperature and maintaining said elevated temperature for a time period sufficient to produce bis-(N,N-dialkylamino)alkyl ether, and (c) recovering the bis-(N,N-dialkylamino)alkyl ether.

In another aspect of the present invention, potassio N,N-dialkylaminoalkoxide is employed instead of sodio N,N-dialkylaminoalkoxide in the above-specified process.

The bis-(N,N-dialkylamino)alkyl ethers produced in accordance with the process of the present invention are useful as catalysts in the production of cellular polyurethanes. One such catalyst, bis[2-(N,N-dimethylamino)-ethyl] ether, is particularly useful in the production of flexible polyurethane foam.

DESCRIPTION OF THE PREFERRED EMBODIMENTS

The reaction according to the process of the present invention is a two-step, "one pot" reaction that can be depicted for the case where the sulfur oxychloro-containing compound is sulfuryl chloride as follows:

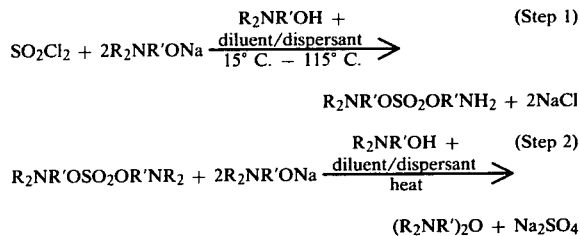

$$SO_2Cl_2 + 2R_2NR'ONa \xrightarrow[15° C. - 115° C.]{R_2NR'OH + \text{diluent/dispersant}} \text{(Step 1)}$$

$$R_2NR'OSO_2OR'NR_2 + 2NaCl$$

$$R_2NR'OSO_2OR'NR_2 + 2R_2NR'ONa \xrightarrow[\text{heat}]{R_2NR'OH + \text{diluent/dispersant}} \text{(Step 2)}$$

$$(R_2NR')_2O + Na_2SO_4$$

wherein R is methyl or ethyl and R' is a bivalent alkylene group having from 2 to 3 carbon atoms.

The sodio dialkylaminoalkoxide reactant can be produced by reacting sodium hydroxide with N,N-dialkylalkanolamine at about 100° C. and removing the water by-product by distillation. The sodio dialkylamino-alkoxide reactant can also be prepared by dissolving sodium metal in N,N-dialkylalkanolamine. Useful sodio dialkylaminoalkoxides include, for example, sodio-2-N,N-dimethylaminoethoxide, sodio 1-N,N-dimethylamino-2-propoxide, sodio 3-N,N-dimethylamino-1-propoxide, sodio 2-N,N-diethylaminoethoxide, sodio 1-N,N-diethylamino-2-propoxide, and sodio 3-N,N-diethylamino-1-propoxide. The potassio dialkylaminoalkoxide reactant can be produced by an analogous method (e.g., by reacting potassium hydroxide with N,N-dialkylalkanolamine and removing the water by-product by distillation). Useful potassio dialkylaminoalkoxides whould include the potassio analogs of the above-listed sodio compounds such as, for example, potassio-2-N,N-dimethylaminoethoxide and potassio 1-N,N-dimethylamino-2-propoxide.

The sodio dialkylaminoalkoxide reactant is utilized in solution with the corresponding dialkylaminoalkanol (characterized by the formula R₂NR'OH, wherein R and R' are defined above) in the reaction mixture. The dialkylaminoalkanol acts as a solvent for the sodio dialkylaminoalkoxide. Thus, for example, sodio 2-N,N-diethylaminoethoxide is used in solution with N,N-diethylethanolamine; sodio 2-N,N-dimethylaminoethoxide is used in solution with N,N-dimethylethanolamine; and sodio 3-N,N-dimethylamino-1-propoxide is used in solution with 3-N,N-dimethylamino-1-propanol. The dialkylaminoalkanol is employed in order to insure that the sodio dialkylaminoalkoxide remains soluble in the reaction mixture during Step 1 of the reaction and does not crystallize out of the mixture. The molar ratio of sodio dialkylaminoalkoxide to the corresponding dialkylaminoalkanol is not narrowly critical and generally ranges from about 1:1 to about 1:3 (preferably from about 1:1.5 to about 1:2.5). The reaction according to the process of the present invention can alternatively be effected by substituting potassio dialkylaminoalkoxide for sodio dialkylaminoalkoxide.

The organic diluent/dispersant which is optionally employed in the process of the present invention can serve several functions. First, it acts as a diluent for the sodio dialkylaminoalkoxide reactant, thereby moderating the rate of the sodio dialkylaminoalkoxide/sulfur oxychloro-containing compound reaction and reducing the likelihood of charring during that reaction. Second, it acts as a dispersant and co-solvent (together with the dialkylaminoalkanol) for the sodio dialkylaminoalkoxide, preventing the crystallization of the sodio dialkylaminoalkoxide during Step 1 of the reaction. Third, it acts as a dispersant for the byproduct sodium chloride, thereby minimizing interference with the stirring of the reaction mixture by the sodium chloride. Fourth, it optionally serves as a "pot-boiler" during recovery of the bis-(N,N-dialkylamino)alkyl ether. Useful diluent/dispersants must both (a) not readily react with the sulfur oxychloro-containing compound when incorporated into the reaction mixture and (b) have a boiling point of at least about 90° C. (preferably at least about 100° C.) at atmospheric pressure. Such a boiling point will insure that the reaction will occur within a commercially acceptable time period since the reflux temperature (and, hence, reaction temperature) that is achievable for the reaction mixture is directly related to the boiling point of the diluent/dispersant. In addition, provided that the boiling point of the diluent/dispersant is at least about 10° C. higher (preferably at least about 20° C. higher) than that of the bis-ether product, it will function as a "pot-boiler" for recovery of the bis-ether. Useful diluent/dispersants include straight-chained hydrocarbons such as n-heptane, n-octane and n-tetradecane; mixed straight-chained, mixed branched-chained and mixed straight-chained/branched-chained hydrocarbons having a number of carbons atoms per molcule of from about 6 to about 30; and ethers such as tetrahydrofuran, dioxane, monoglyme and diglyme.

The amount of diluent/dispersant employed according to the process of the present invention can vary widely depending upon the particular reactants and diluent/dispersant used. Generally, the diluent/dispersant is present in an amount ranging from about 0 to about 60 (preferably 40 to 60) weight percent based on the amount of sodio N,N-dialkylaminoalkoxide and N,N-dialkylaminoalkoanol employed in the reaction mixture. When the N,N-dialkylaminoalkanol is employed in a relatively large amount (i.e., an amount such that the molar ratio of sodio N,N-dialkylaminoalkoxide to N,N-dialkylaminoalkanol ranges from about 1:2.5 to about 1:3), the reaction can be effected without employing a diluent/dispersant.

The sulfur oxychloro-containing compound useful in the process of the invention is a liquid which is added in an amount of from about 0.10 to about 0.50 (preferably from about 0.20 to about 0.35) moles per mole of sodio N,N-dialkylaminoalkoxide reactant.

The limits on the reaction time for the process of the invention are not narrowly critical and can vary over a wide range. Because Step 1 of the reaction proceeds rapidly upon addition of the sulfur oxychloro-containing compound to the reactor, the time period required for Step 1 is limited solely by the addition rate that can be achieved while maintaining the temperature of the reaction mixture within the specified limits. Generally, a suitable time period for Step 1 is from about 0.5 to about 10 hours (preferably from about 0.5 to about 2 hours). Byproduct sodium chloride will separate from the reaction mixture during the first reaction step. In Step 2 of the reaction, the reactants are heated to an elevated temperature such as, for example, from about 80° C. or lower to about 190° C. or higher (preferably from about 100° C. to about 130° C.; most preferably abut 115° C.) and maintained at said elevated temperature for a time period sufficient to produce the bis-(N,N-dialkylamino)alkyl ether product. The time period required for Step 2 is generally from about 1.5 to about 12 hours (preferably from about 1.5 to about 3 hours).

Atmospheric pressure is generally employed in the process of the invention, although super- or sub-atmospheric pressures can be used if desired for some purpose.

Recovery of the bis(N,N-dialkylamino)alkyl ether product can be effected by any known method. The preferred method involves a stripping distillation at the end of the reaction sequence. Using such a technique, the process is clearly a "one-pot" process since product recovery can be made directly from the reactor.

As indicated above, the process of the present invention is useful in preparing bis(N,N-dialkylamino)alkyl ethers characterized by the formula $(R_2NR')_2O$ wherein R and R' are defined above. Bis(N,N-dialkylamino)alkyl ethers encompassed by the formula include: bis[beta(N,N-dimethylamino)ethyl] ether, bis[beta(N,N-dimethylamino)-1-methylethyl] ether, bis[3-N,N-dimethylamino)propyl] ether, bis[beta(N,N-diethylamino)ethyl] ether, and bis[beta(N,N-diethylamino)-1-methylethyl] ether. The preferred bis(N,N-dialkylamino)alkyl ether is BDMEE. Other tertiary amine-containing bisethers, not encompassed by the above formula, that may be produced according to the process of the instant invention include:

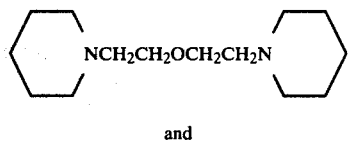

and

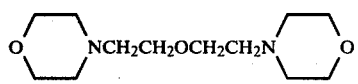

As has been indicated above, such ethers are useful as catalysts in the production of cellular polyurethanes.

The following Examples are illustrative of, but are not intended to limit, the present invention.

EXPERIMENTAL

The following experimental description illustrates the present invention. In the experimental description, the following abbreviations are used:

| Abbreviation | Meaning | |
|---|---|---|
| BDMEE | bis[2-(N,N-dimethylamino)ethyl]ether | |
| percent | weight percent | |
| mm. | millimeter | |
| Diluent I | A hydrocarbon mixture consisting essentially of normal paraffins. A typical composition contains the following: | |
| | Paraffin | Weight Percent |
| | Normal Paraffin $C_{13}$ | <4 |
| | Normal Paraffin $C_{14}$ | 20–25 |
| | Normal Paraffin $C_{15}$ | 42–47 |
| | Normal Paraffin $C_{16}$ | 23–28 |
| | Normal Paraffin $C_{17}$ | 5–10 |
| | Normal Paraffin $C_{18}$ and higher | <3 |

EXAMPLE I

Synthesis of BDMEE Using Sulfuryl Chloride

A 3-necked, 2-liter reactor was provided with a mechanical stirrer, thermometer, feed tank and reflux condenser connected to a source of a dry nitrogen atmosphere. The reactor was also equipped with a colling bath for controlling the temperature of the reaction mixture.

To the reactor was added a mixture of 177.8 grams (1.6 moles) of sodio 2-(N,N-dimethylamino)-ethoxide, 214.5 grams (2.4 mols) of N,N-dimethylethanol-amine and 267 grams of Diluent I. The mixture was rapidly cooled to about 25° C. with stirring. Sulfuryl chloride (54.0 grams, 0.4 mole) was added over a one hour period with stirring and cooling in order to maintain the reaction mixture temperature between 24° C. and 29° C. By-product sodium chloride separated during the addition. Upon completion of the addition of sulfuryl chloride, the mixture was maintained at between 24° C. and 29° C. with stirring for one hour. The mixture was then heated to 115° C. and maintained at this temperature for 2.5 hours with stirring under a dry nitrogen atmosphere. The reaction product was distilled through an entrainment separator at a pressure of 50 mm. at the beginning of the distillation and a pressure of 5 mm at the end to produce a distillate consisting of N,N-dimethylethanolamine and the BDMEE product in addition to a small amount of Dilueht I. Redistillation of this broad-range distillate though a 35-tray Oldershaw column provided BDMEE as a fraction boiling at 88° C. at 25 mm. The yield of BDMEE was between 54 and 57 percent, based on the sulfuryl chloride employed.

EXAMPLE 2

Synthesis of BDMEE Using Thionyl Chloride

Using the apparatus and procedure of Example 1, a reaction was carried out using identical quantities of all reactants except that 47.6 grams (0.4 moles) of thionyl chloride was substituted for the 0.4 moles of sulfuryl chloride. BDMEE was isolated using the procedure of Example 1. The yield of BDMEE was 35 percent, based on the thionyl chloride employed.

EXAMPLE 3

Synthesis of BDMEE Using Chlorosulfonic Acid.

A 4-necked, 2-liter reactor was provided with a mechanical stirrer, thermometer, feed tank and reflux condenser connected to a source of a dry nitrogen atmosphere. The reactor was also equipped with a cooling bath for controlling the temperature of the reaction mixture.

To the reactor was added a mixture of 166.7 grams (1.5 moles) of sodio 2-(N,N-dimethylamino)ethoxide, 264.6 grams (2.97 moles) of N,N-dimethylethanolamine and 250 grams of Diluent I. The mixture was rapidly cooled to about 25° C. with stirring. Chlorosulfonic acid (52.4 grams, 0.45 moles) was added over a one hour period with stirring and cooling in order to maintain the reaction temperature between 25° C. and 30° C. Upon completion of the addition of the chlorosulfonic acid, the mixture was maintained at 23° C. for two hours. The mixture was then heated to 115° C. and maintained at this temperature for 3 hours with stirring under a dry nitrogen atmosphere. The reaction product was distilled through an entrainment separator under reduced pressure with stirring to provide a broad-range distillate. Redistillation of the broad-range distillate through a 30-tray Oldershaw column provided BDMEE as a fraction boiling at 86° C. to 88° C. at 25 mm. The yield of BDMEE was 79 percent, based on chlorosulfonic acid employed.

What is claimed is:

1. A process for producing bis-(N,N-dialkylamino)-alkyl ether having the formula $(R_2NR')_2O$, wherein R is a methyl or ethyl group and R' is a bivalent alkylene group having from 2 to 3 carbon atoms, which comprises:
   (a) reacting sodio N,N-dialkylaminoalkoxide of the formula $R_2NR'ONa$, wherein R and R' are defined above, with a sulfur oxychloro-containing compound selected from the group consisting of slfuryl chloride, thionyl chloride and chlorosulfonic acid in an amount of from about 0.10 to about 0.50 moles of said sulfur oxychloro-containing compound per mole of sodio N,N-dialkylaminoalkoxide at a temperature of from about 15° C. to about 115° C. in the presence of:
      (I) an organic diluent/dispersant in an amount ranging from 0 to about 60 weight percent based on the amount of sodio N,N-dialkylaminoalkoxide and N,N-dialkylaminoalkanol employed, and
      (II) an N,N-dialkylaminoalkanol of the formula $R_2NR'OH$, wherein R and R' are defined above, that is present in an amount such that the molar ratio of sodio N,N-dialkylaminoalkoxide to N,N-dialkylaminoalkanol ranges from about 1:1 to about 1:5,
   to produce an intermediate reaction product mixture,
   (b) heating the intermediate reaction product mixture from step (a) to an elevated temperature and maintaining said elevated temperature for a time period sufficient to produce bis(N,N-dialkylamino)alkyl ether, and
   (c) recovering the bis-(N,N-dialkylamino)alkyl ether.

2. The process of claim 1 wherein the sulfur oxychloro-containing compound is sulfuryl chloride.

3. The process of claim 1 wherein the sulfur oxychloro-containing compound is thionyl chloride.

4. The process of claim 1 wherein the sulfur oxychloro-containing compound is chlorosulfonic acid.

5. The process of claim 1 wherein the amount of sulfur oxychloro-containing compound ranges from about 0.20 to about 0.35 moles per mole of sodio N,N-dialkylaminoalkoxide.

6. The process of claim 1 wherein (a) is carried out at a temperature of from about 25° C. to about 30° C.

7. The process of claim 1 wherein the organic diluent/dispersant is employed in an amount of from about 40 to about 60 weight percent based on the amount of sodio N,N-dialkylaminoalkoxide and N,N-dialkylaminoalkanol employed.

8. The process of claim 1 wherein the molar ratio of sodio N,N-dialkylaminoalkoxide to N,N-dialkylaminoalkanol is from about 1:1.5 to about 1:2.5.

9. The process of claim 1 werein the bis-(N,N-dialkylamino)alkyl ether is bis[beta-(N,N-dimethylamino)ethyl] ether, the sodio N,N-dialkylaminoalkoxide is sodio 2-N,N-dimethylaminoethoxide, the N,N-dialkylaminoalkanol is N,N-dimethylethanol amine, and the diluent/dispersant is a mixture of aliphatic hydrocarbons having from about 6 to about 30 carbon atoms.

10. The process of claim 1 wherein the bis-(N,N-dialkylamino)alkyl ether is bis[beta-(N,N-diethylamino)ethyl] ether, the sodio N,N-dialkylaminoalkoxide is sodio 2-N,N-diethylaminoethoxide, the N,N-dialkylaminoalkanol is N,N-diethylethanolamine, and the diluent/dispersant is a mixture of aliphatic hydrocarbons having from about 6 to about 30 carbon atoms.

11. The process of claim 1 wherein the bis-(N,N-dialkylamino)alkyl ether is bis[3-(N,N-dimethylamino)propyl] ether, the sodio N,N-dialkylaminoalkoxide is sodio 3-N,N-dimethylamino-1-propoxide, the N,N-dialkylaminoalkanol is 3-N,N-dimethylamino-1-propanol, and the diluent/dispersant is n-octane.

12. The process of claim 1 wherein the bis-(N,N-dialkylamino)alkyl ether is bis[beta-(N,N-dimethylamino)-1-methylethyl] ether, the sodio N,N-dialkylaminoalkoxide is sodio 1-N,N-dimethylamino-2-propoxide, the N,N-dialkylaminoalkanol is 1-N,N-dimethylamino-2-propanol, and the diluent/dispersant is a mixture of aliphatic hydrocarbons having from about 6 to about 30 carbon atoms.

13. A process which comprises:
   (a) reacting sodio 2-N,N-dimethylaminoethoxide with a sulfur oxychloro-containing compound selected from the group consisting of sulfuryl chloride, thionyl chloride and chlorosulfonic acid in an amount of from about 0.10 to about 0.50 moles of said sulfur oxychloro-containing compound per mole of sodio 2-N,N-dimethylaminoethoxide at a temperature of from about 25° C. to about 30° C. in the presence of:
      (I) an organic diluent/dispersant in an amount ranging from about 40 to about 60 weight percent based on the amount of sodio 2-N,N-dimethylaminoethoxide and N,N-dimethylethanolamine, and
      (II) N,N-dimethylethanolamine in an amount sufficient to produce a molar ratio of sodio 2-N,N-dimethylaminoethoxide to N,N-dimethylethanolamine of from about 1:1 to about 1:5,
   for a time period sufficient to produce an intermediate reaction product mixture,
   (b) heating the intermediate reaction product mixture from step (a) to an elevated temperature and maintaining said elevated temperature for a time period sufficient to produce bis[2-(N,N-dimethylamino)ethyl] ether, and
   (c) recovering the bis[2-N,N-dimethylamino)ethyl] ether.

14. The process of claim 13 wherein the sulfur oxychloro-containing compound is sulfuryl chloride.

15. The process of claim 13 wherein the sulfur oxychloro-containing compound is thionyl chloride.

16. The process of claim 13 wherein the sulfur oxychloro-containing compound is chlorosulfonic acid.

17. A process for producing bis-(N,N-dialkylamino)alkyl ether having the formula $(R_2NR')_2O$, wherein R is a methyl or ethyl group and R' is a bivalent alkylene group having from 2 to 3 carbon atoms, which comprises:
   (a) reacting potassio N,N-dialkylaminoalkoxide of the formula $R_2NR'OK$, wherein R and R' are defined above, with a sulfur oxychloro-containing compound selected from the group consisting of sulfuryl chloride, thionyl chloride and chlorosulfonic acid in an amount of from about 0.10 to about 0.50 moles of said sulfur oxychloro-containing compound per mole of potassio N,N-dialkylaminoalkoxide at a temperature of from about 15° C. to about 115° C. in the presence of:
      (I) an organic diluent/dispersant in an amount ranging from 0 to about 60 weight percent based on the amount of potassio N,N-dialkylaminoalkoxide and N,N-dialkylaminoalkanol employed, and (II) an N,N-dialkylaminoalkanol of the formula R₂NR'OH, wherein R and R' are defined above, that is present in an amount such that the molar ratio of potassio N,N-dialkylaminoalkoxide to N,N-dialkylaminoalkanol ranges from about 1:1 to about 1:3, to produce an intermediate reaction product mixture, (b) heating the intermediate reaction product mixture from step (a) to an elevated temperature and maintaining said elevated temperature for a time period sufficient to produce bis-(N,N-dialkylamino)alkyl ether, and (c) recovering the bis-(N,N-dialkylamino)alkyl ether.

* * * * *